(12) United States Patent
Spalten

(10) Patent No.: US 6,273,720 B1
(45) Date of Patent: Aug. 14, 2001

(54) DENTAL IMPLANT SYSTEM

(76) Inventor: Robert Spalten, One Rockefeller Plz., Suite 2221, New York, NY (US) 10020

( * ) Notice: Subject to any disclaimer, the term of this patent is extended or adjusted under 35 U.S.C. 154(b) by 0 days.

(21) Appl. No.: 09/294,560

(22) Filed: Apr. 20, 1999

(51) Int. Cl.[7] ................................................ A61C 8/00
(52) U.S. Cl. ......................... 433/173; 433/172; 433/176; 433/201.1
(58) Field of Search .................................. 433/172, 173, 433/174, 175, 176, 201.1

(56) References Cited

U.S. PATENT DOCUMENTS

| | | | |
|---|---|---|---|
| 4,062,119 | * 12/1977 | Linkow et al. | 433/176 |
| 4,424,037 | * 1/1984 | Ogino et al. | 433/173 |
| 5,006,070 | * 4/1991 | Komatsu | 433/173 |
| 5,030,095 | * 7/1991 | Niznick | 433/173 |
| 5,049,074 | * 9/1991 | Otani et al. | 433/173 |
| 5,052,930 | * 10/1991 | Lodde et al. | 433/173 |
| 5,215,460 | * 6/1993 | Perry | 433/173 |
| 5,417,570 | * 5/1995 | Zuest et al. | 433/173 |
| 5,636,989 | * 6/1997 | Somborac et al. | 433/173 |
| 5,725,377 | * 3/1998 | Lemler et al. | 433/173 |
| 5,730,598 | * 3/1998 | Story et al. | 433/173 |
| 5,759,033 | * 6/1998 | Elia | 433/201.1 |
| 5,759,034 | * 6/1998 | Daftary | 433/173 |
| 5,782,918 | * 7/1998 | Klardie et al. | 433/173 |
| 5,904,483 | * 5/1999 | Wade | 433/173 |

* cited by examiner

Primary Examiner—John J. Wilson
(74) Attorney, Agent, or Firm—E. Lieberstein

(57) ABSTRACT

A dental implant system including an implant having an incisal portion for insertion into a alveolar receptor site formed in the jawbone to receive the implant, a collar having a beveled shape extending superiorly from the incisal portion with a smooth polished surface, a threadless cavity extending from the occlusal end of the implant partially into said embedded incisal portion with the cavity having a recessed groove adjacent the proximal end of the incisal portion, a removable healing cap adapted to be placed into the threadless cavity of said implant with said healing cap having a resilient shoulder projecting therefrom to engage said groove for forming a sealed interlock during an extended healing period and a single post abutment member for insertion into the threadless cavity of the implant after removal of the healing cap. An alternative embodiment of the implant system includes an implant having an incisal section with a vertical height of less than about 6mm for insertion into a very shallow bone receptor site formed in the jawbone of the patient, a plurality of projections laterally extending from a position near the apical end of the implant in a spider like arrangement so that they initially cover a broad subperiosteal surface adjacent mucosal tissue to give the implant lateral stability against lateral forces.

15 Claims, 4 Drawing Sheets

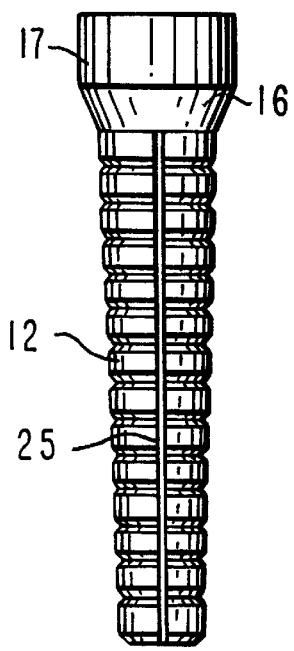
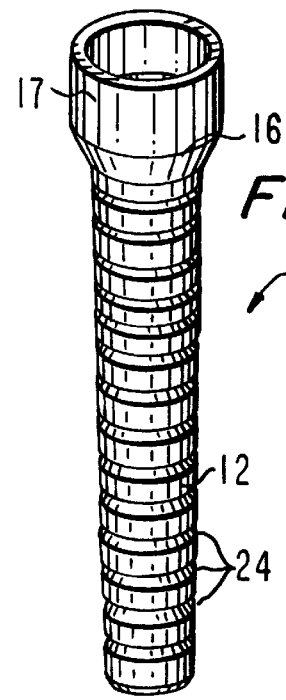
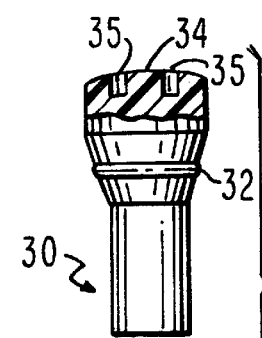
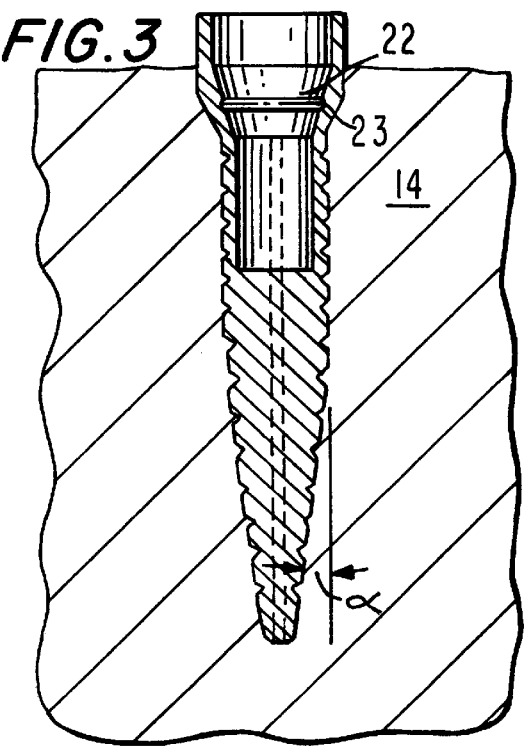
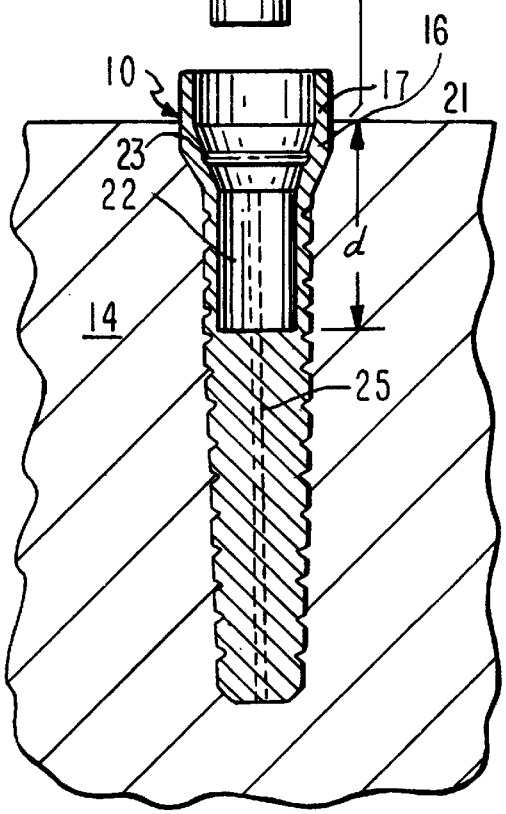
FIG. 1A
FIG. 1
FIG. 2
FIG. 3

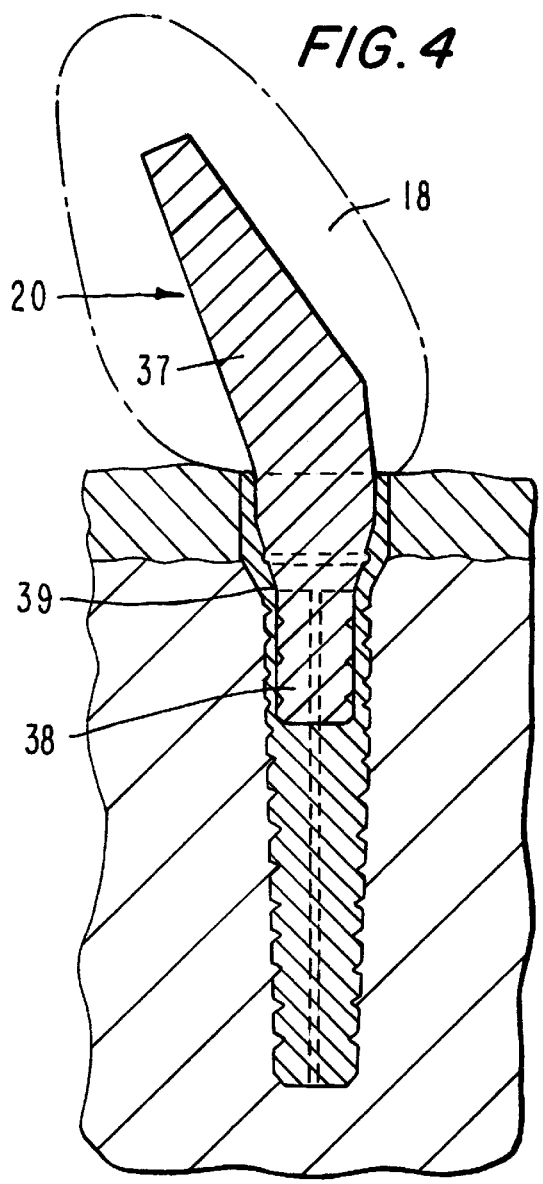
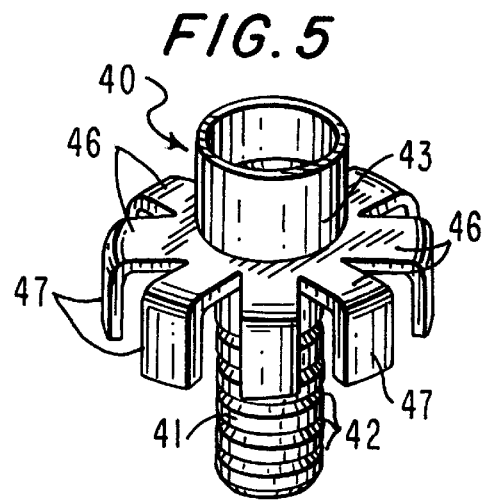
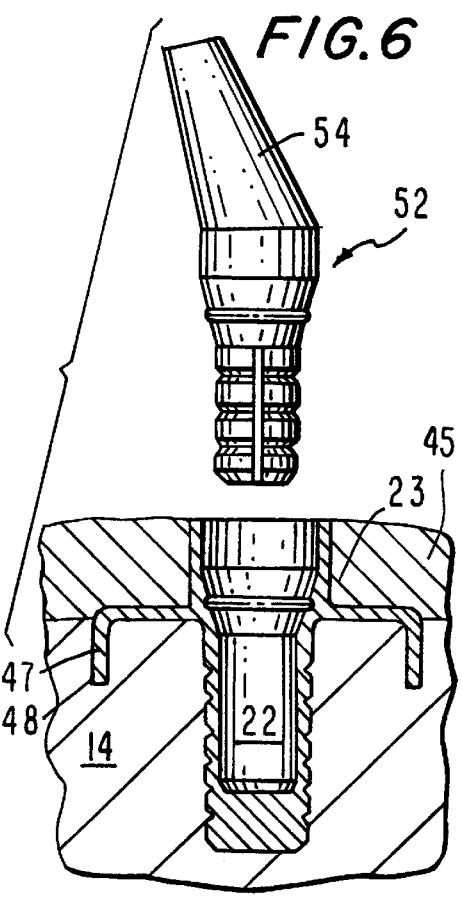
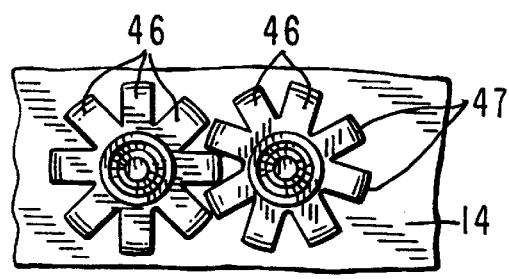

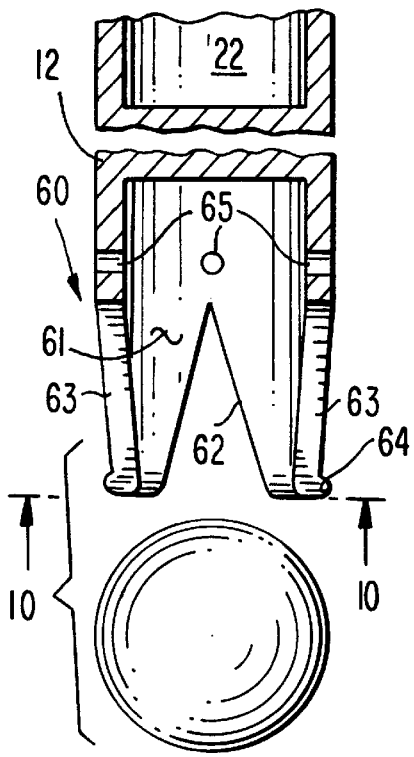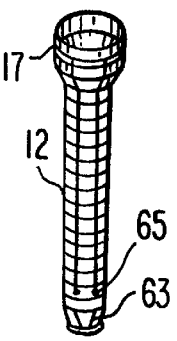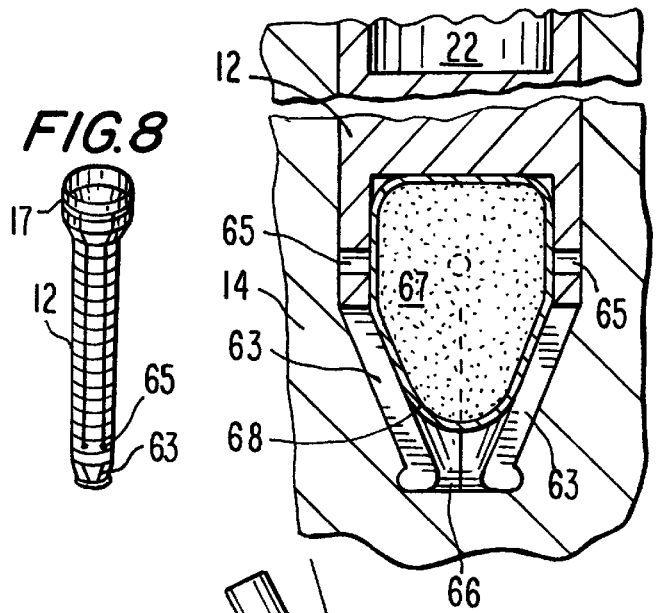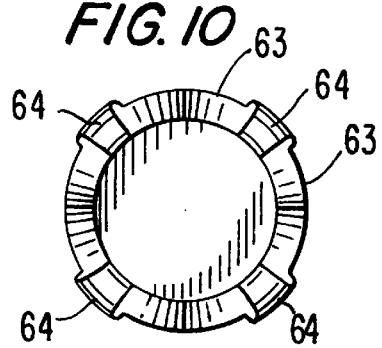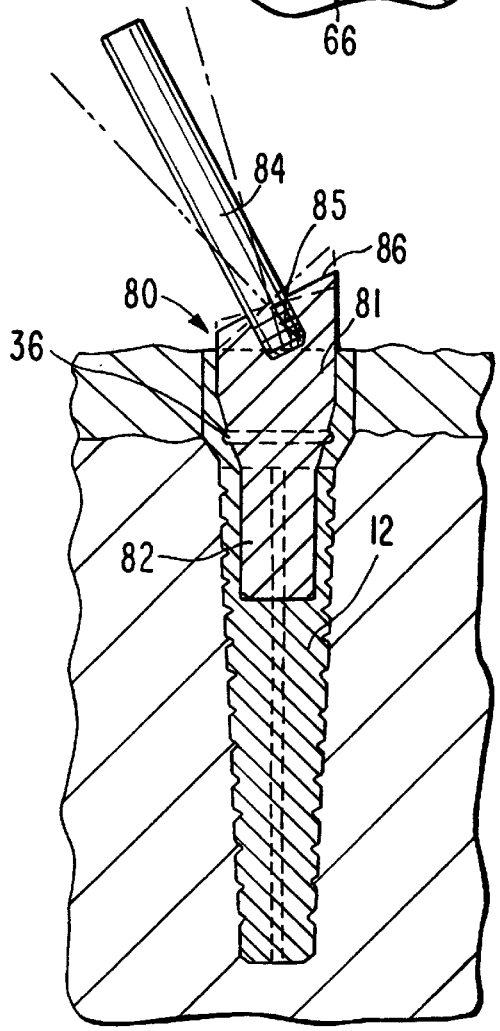

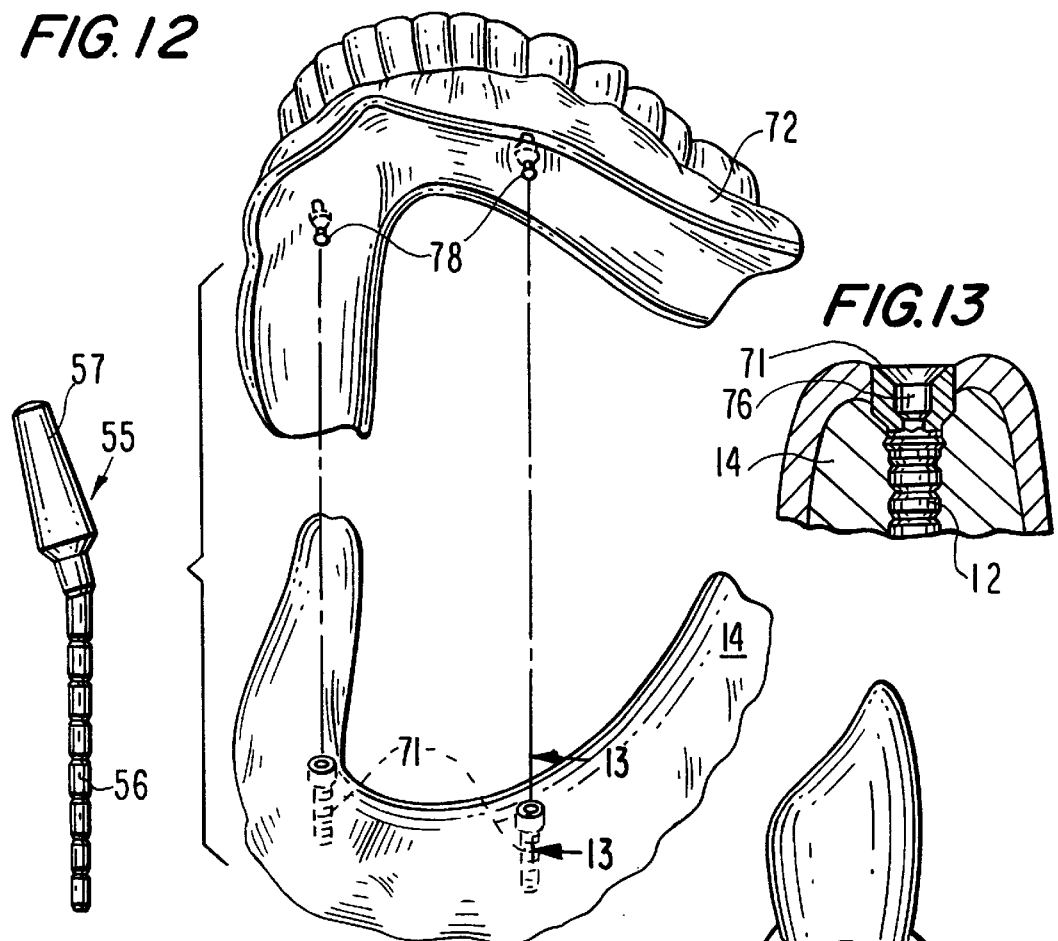
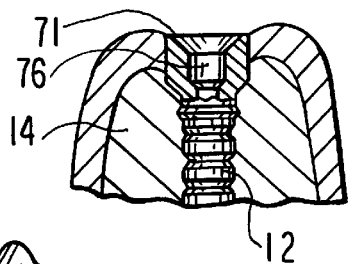
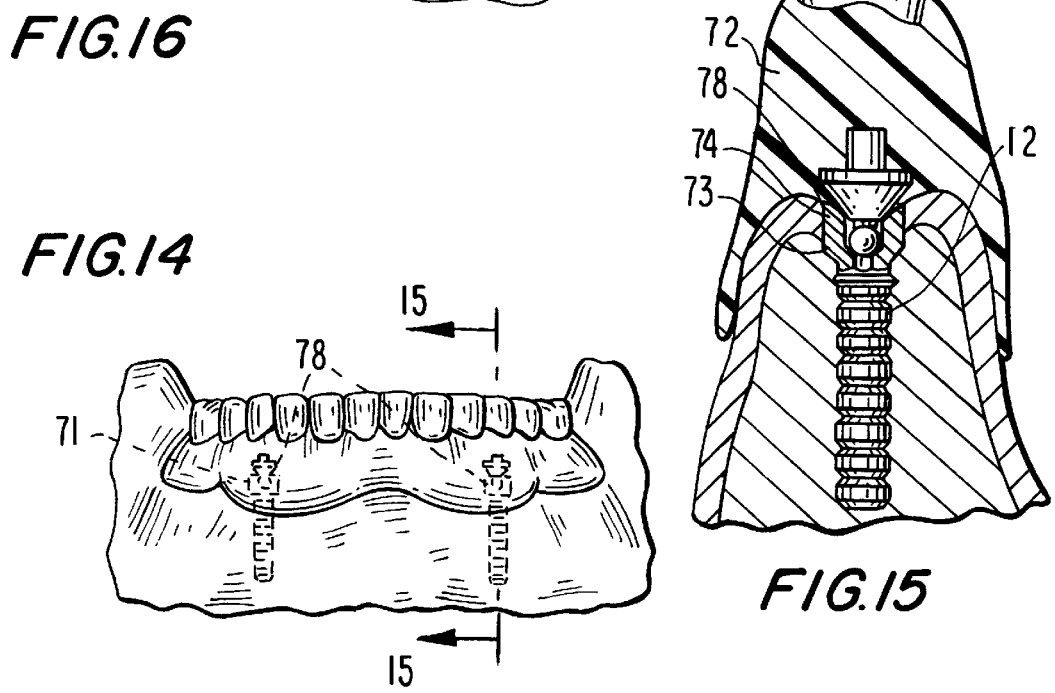

DENTAL IMPLANT SYSTEM

FIELD OF INVENTION

This invention relates to an improved dental implant system which minimizes or eliminates laboratory fees and accelerates healing in a shorter time period with greater predictability compared to conventional implant systems.

BACKGROUND OF THE INVENTION

A dental implant is a submergible structure which is inserted in the alveolar cavity of the jawbone to permit attachment of a dental prosthesis to the implant in an edentulous region. The implant requires a healing period of up to nine months to assure bone ingrowth and clinical ossiointergration at the bone implant interface. Once the healing period is over and the implant is firmly anchored to new bone, the mucosal gum tissue above the implant is penetrated for attachment of an upper post portion to which an artificial dental prosthesis is connected.

Conventional dental implants utilize a plurality of components commonly referred to as abutments which in combination with the embedded implant form the implant system. The abutments of a conventional implant system are externally and internally threaded to permit the components to be removably interconnected to one another. The proximal end of the abutments are typically shaped in the configuration of an hexagonal nut so that a wrench may be used to interconnect the abutment to the implant. The implant also contains a threaded recess to receive an abutment and has a projection at its occlusal end which is also in an hexagonal configuration. The implant may also be externally threaded to facilitate a self-tapping insertion of the implant into the cortical bone substructure.

The array of interconnecting abutments of a conventional implant system increase the installation expense of the implant and may necessitate the assistance of an outside dental laboratory to provide the component parts. More importantly, it has now been clinically established that the use of multi-threaded interconnecting abutments unavoidably leave clearance spaces or gaps at the interface between the internal and external threads of the implant and the interconnecting abutments. These gaps represent hollow crevices which allow for microbial leakage and also act as a trap for bacteria permitting microbial colonization at the juncture between the fittings. Microbial leakage can also cause inflammatory reactions in the peri-implant soft tissue. In addition, the use of many abutment components increase the procedure time and cause complications based upon the various parts needed. Furthermore there is an increased likelihood of the many parts not fitting accurately or loosening up from the occlusal forces during chewing which can result in excessive wear and breakdown.

In addition the post abutment may need to be placed at an angle with respect to the embedded implant in order to align the artificial dental prosthesis with the other teeth of the patient. To achieve this the post abutment is either bent after installation or is preangulated. Bending the post after installation is contraindicated and can cause fatigue and breakage. Although the use of a preangulated post is preferred this currently requires at least one additional screw-like member to secure the post to the implant. This complicates the design of the preangulated post since the design must account for how the screw is to be fastened through the post to the implant. Moreover if the post abutment, screw and implant are all threaded to facilitate their interconnection this will lead to the problem of microbial leakage referred to above.

The implant system of the preferred embodiment of the present invention is a two component system utilizing a narrow gauge implant which is preferably tapered and precisely contoured to press fit into the bone receptor site. A healing cap is removably inserted into a non-threaded cavity formed in the implant to form a seal within the cavity so as to permit healing of the implant without any potential for microbial leakage. Upon removal of the cap a single post abutment component is placed into the cavity for connecting the implant to a dental prosthesis. Since the implant is non-threaded the circumference of the implant may be significantly narrower in size relative to the circumference of the conventional threaded implant. In addition, the single post abutment is seated into the implant which permits it to be preangulated at an angle of from 0° to 30° to achieve parallelism with adjoining implant posts or other abutments without complicating its design. Once a preangulated post is selected with the desired preangulation it is fitted into the implant and then turned relative to the longitudinal axis of the implant to achieve the desired alignment. Thereafter the post is cemented in place to the implant. A plurality of horizontally spaced serrations are preferably formed around the circumference of the implant with the serrations spaced a fixed distance apart and extending over the entire vertical height of the embedded implant or a section thereof.

In another embodiment of the present invention the post abutment includes a shaft extending from the post abutment at any desired angle relative to the longitudinal axis of the implant. In this embodiment the desired angle is formed by connecting a threaded shaft into a threaded opening in the post abutment which can be done after the post abutment is seated in the implant. The threaded opening may be formed at any desired predetermined angle with the longitudinal axis of the implant thereby establishing a predetermined angle of inclination for the threaded shaft relative to the longitudinal axis of the implant.

In another two-component embodiment of the implant system of the present invention the vertical height of the implant may be shortened to a length of less than about 6 mm which facilitates insertion into a very shallow bone receptor site. In this embodiment the implant includes lateral projections extending from a position near the apical end of the implant to give the implant lateral stability. The use of a very short implant having lateral projecting arms at the occlusal end in a spider like arrangement permits the implant to avoid contact with the maxillary sinus or the mandibular nerve and may be used in the posterior portion of the mandible and maxilla in cases where minimum vertical height of bone is available. Two implants of this type having lateral projections in a spider like arrangement may also be inserted into the bone in tandem to provide additional strength and may be aligned so that the projections interdigitate. The use of two implants of this type in tandum is particularly suited for use where bone structure is minimal in the labialpalatal dimension in a posterior portion of the mandible or maxilla.

Yet another embodiment of the invention is a unitary narrow gauge implant having an integrated abutment post forming a unitary solid implant structure containing a post abutment for use in a posteria region of the mandible and/or maxilla where the jawbone is narrow. This implant is of a very narrow gauge with an extended length of over 18 mm and preferably between 18–22 mm. Two narrow gauge implants of this type may be used in tandem.

An additional embodiment of the present invention is an implant for use with a denture which permits a denture to be removably attached to either the upper or lower jawbone and to maintain the denture in a fixed position within a patients mouth.

In yet another embodiment of the present invention the distal end of the implant body is formed with a hollow interior adapted for the insertion of a bone morphogenic protein which is known to facilitate bone osseointegration. The distal end of the implant body surrounding the hollow area is defined by a plurality of projections extending lengthwise in a direction substantially parallel to the longitudinal axis of the implant permitting the distal end to be crimped so as to form an enclosure for the insertion of a bone morphogenic protein material composition.

SUMMARY OF THE INVENTION

One embodiment of the implant system of the present invention includes an implant having a tapered apical portion for insertion into an alveolar receptor site formed in the jawbone to receive the implant, a collar extending superiorly from the incisal portion with the collar having a beveled section, a threadless cavity extending through said collar and partially into the apical portion of the embedded implant, a recessed groove formed in the collar of the implant, a removable healing cap adapted to be placed into the threadless cavity of said implant with said healing cap having a resilient shoulder projecting therefrom in alignment with said recessed groove so as to form a sealed interlock upon insertion of the healing cap in said cavity and a single post abutment member for insertion into the threadless cavity of the implant after removal of the healing cap. The single abutment member may be preangulated at an angle of between 0° to 30° relative to the longitudinal axis of the implant to achieve parallelism with adjoining teeth in the mouth of the patient. A plurality of serrations are preferably formed around the circumference of the implant horizontally spaced apart from one another with the serrations extending over a section of the vertical height of the embedded portion of the implant to permit a plasma sprayed coating of hydroxyl apatite to be readily seated therein.

Another embodiment of the present invention comprises a dental implant having an apical portion for insertion into a very shallow bone receptor site formed in the jawbone with a vertical height corresponding to a length of less than about 8 mm, a plurality of projections laterally extending from a position near the apical end of the implant in a spider like arrangement for engaging the jawbone at the surface adjacent to mucosal tissue to give the implant lateral stability, a threadless cavity extending from the apical end of the implant at least partially through the embedded implant, a removable healing cap for placement into said cavity and a post abutment member for insertion into the cavity after removal of the healing cap.

Yet another embodiment of the present invention comprises a dental implant formed as a solid integrated single structure having an abutment post extending from a narrow gauge apical portion with said structure having a length of between 18–22 mm for insertion into a receptor site of a narrow jawbone.

A further embodiment of the present invention comprises a dental implant designed to be interconnected to a denture to permit the denture to be removably attached to the upper or lower jawbone of a patient, said implant comprising an incisal portion for insertion into an alveolar receptor site formed in the upper or lower jawbone to receive the implant, a partial cavity formed in the implant extending from the apical end with a portion near the occlusal surface having a substantially spherical geometry for forming a female coupling adapted to receive a complementary male abutment extending from a denture with said complementary male abutment being in alignment with the cavity of the implant when the denture is seated over the jawbone, said complementary male abutment having a corresponding spherical shape and size for insertion into the socket of the implant.

BRIEF DESCRIPTION OF THE DRAWINGS

Other features and advantages of the present invention will become apparent from the following detailed description of the invention when read in conjunction with the accompanying drawings of which:

FIG. 1 is a view in perspective of a preferred embodiment of the implant of the present invention;

FIG. 1A is a modified version of the implant of FIG. 1;

FIG. 2 is an exploded cross sectional view of the implant of FIG. 1 with the implant shown embedded in a bone receptor site of a jawbone in combination with a healing cap which is removably inserted into the implant to permit the implant to heal before a post abutment as shown in FIG. 4 or FIG. 11 is substituted for the healing cap and cemented into the implant;

FIG. 3 is a cross sectional view of a modified embodiment of the implant shown in FIG. 2 having a tapered incisal body at least extending over the lower distal end region thereof;

FIG. 4 is a cross sectional view of the implant system of FIG. 2 in which the healing cap is removed and replaced with a preangulated post abutment over which a dental prosthesis is formed to match adjacent teeth;

FIG. 5 shows an alternative embodiment of an implant system in accordance with the present invention;

FIG. 6 is an exploded cross sectional view of the implant of FIG. 5 with the implant shown embedded in a bone receptor site of a jawbone in combination with a healing cap which is removably inserted into the implant to permit the implant to heal before a post abutment as shown in connection with FIG. 4 or FIG. 11 is substituted for the healing cap and is cemented into the implant;

FIG. 7 is a top view of a pair of the FIG. 5 type implants inserted into the jawbone with the arms from each of the implants arranged in an interdigitating relationship relative to one another;

FIG. 8 is a perpective view of another embodiment of the implant system of the present invention;

FIG. 9 is an exploded view in cross section of the distal end of the implant shown in FIG. 8;

FIG. 10 is a bottom view of the distal end of the implant of FIG. 9 taken along the lines 10—10 of FIG. 9;

FIG. 11 is another view of the distal end of the implant of FIG. 8 after crimping the slitted ends thereof so as to form an enclosure adapted for insertion of a conventional bone morphogenic protein;

FIG. 12 is a perspective view of yet another embodiment of the implant system of the present invention adapted for interconnection to a denture;

FIG. 13 is an enlarged cross sectional view of one of the implants shown in FIG. 12;

FIG. 14 shows the denture of FIG. 12 affixed to the jawbone through the implants;

FIG. 15 is a cross sectional view taken along the lines 15—15 of FIG. 14;

FIG. 16 shows another implant design of the present invention with the implant representing a solid integrated body having a post abutment extending therefrom; and FIG. 17 is a cross sectional view of yet another embodiment of the implant system of FIG. 2 in which the healing cap is removed and replaced with a post abutment adapted to receive a threaded shaft which will extend from the post abutment in a given preangulated direction over which a dental prosthesis is formed to match adjacent teeth.

DETAILED DESCRIPTION OF THE PREFERRED EMBODIMENTS

Referring now to FIGS. 1–4 which correspond to a first preferred embodiment of the implant system of the present invention. As shown in FIGS. 1–3 the implant 10 comprises a narrow gauge body 12, as narrow as 2.8 mm which is press fitted into a receptor site formed in the jawbone 14 of a dental patient. Before installation of the implant 10 an incision is made in the gum tissue of the patient and the underlying bone is exposed. A drill having a drill bit of a configuration matching the configuration of the implant is used to bore a hole in the jawbone 14 of a size slightly smaller than the circumference of the implant body 12. This permits the implant 10 to be press fitted into the bored hole. The implant 10 should be composed of a biocompatible material preferably of titanium metal although any other biocompatible material may be used. Before the implant is press fitted into the bored hole a duplicate "test" or "try in" implant of slightly smaller diameter may be inserted into the bored hole to assure accuracy in fit. The duplicate "test" or "try in" implant may fit relatively loosely. The test implant should be highly polished and may have a head or knob (not shown) at the occlusal end thereof so that it may be easily retrieved before the implant 10 is press fitted into the bore.

The implant body 12 may be tapered as shown in FIG. 3 to facilitate its insertion into the jawbone 14 of the patient. This is particularly important for insertion into the posterior region of the mandible and maxilla where bone structure is minimal. Moreover, in cases where bone structure tapers downwardly which is usually the case for older patients which have lost considerable bone the implant taper may progress to form a relatively substantial tapered angle "α" at the lower distal end 15 of the shaft 12 as shown in FIG. 3. The taper angle "α" at the lower distal end 15 of the implant can be as much as 10° to 15°.

The implant 10 has a beveled collar 16 extending superiorly from the shaft portion 12 of the implant 10 and a substantially upright section 17 of substantially cylindrical geometry at its proximal end. The beveled collar may be somewhat thicker in circumference at the occlusal surface abutting the porcelain superstructure 18 surrounding the post abutment 20 as shown in FIG. 4. The beveled collar 16 and the upright section 17 of the implant 10 may have a smooth polished exterior surface.

A threadless cavity 22 is formed within the interior of the implant 10 extending from its proximal surface partly into the body of the implant 10, i.e. a predetermined distance "d" beneath the occlusal surface 21 of the jawbone. The cavity 22 includes an annular recessed groove 23 formed around the beveled collar 16 preferably where the collar is relatively thick. The exterior of the implant body 12 should preferably have a plurality of serrations 24 which are spaced longitudinally apart along the vertical height of the implant 10 to facilitate the seating of a plasma sprayed coating of hydroxyl apatite "HA" before the implant 10 is press fitted into the jawbone 14. The coating of HA may have a thickness of up to 50 microns to increase bony apposition at the interface between the implant 10 and bone 14. In addition, a substantial vertical relief groove 25 as shown in FIG. 1A and 2 may be formed extending along the exterior of the implant body 12.

Before the gingival tissue is replaced a healing cap 30, as shown in FIG. 2, is inserted into the cavity 22 of the implant 10. The healing cap 30 is an important attribute of the implant system of the present invention and is designed as a plug to permit the implant 10 to heal while clinical ossiointergration occurs at the bone implant interface over a predetermined healing period. During this healing period microbial leakage into the implant 10 is minimized by designing the healing cap 30 to also function as a seal. The healing cap 30 is removably inserted into the cavity 22 of the implant 10 without the complications of using multi-abutment components or tooling. The healing cap 30 is composed of a resilient plastic material having an annular shoulder 32 which snaps into the complementary annular recessed groove 23 of the cavity 22 thereby forming an interlocking seal. This secures the cavity 22 with the plug functioning to prevent microbial leakage. The healing cap 30 has a domed top 34 with two or more depressed areas 35 designed to permit a gripping tool such as a pair of conventional pliers to be used to pull the healing cap 30 out from the cavity 22 after completion of an adequate healing period. Because of the resiliency of the plastic composition of the cap 30, the cap 30 readily disengages from the cavity 22.

Upon removal of the healing cap 30 a post abutment 20, as shown in FIG. 4, is placed into the open cavity 22. The post abutment 20 has a proximal end 37, a distal end 38 seated in the implant 12 and an annular shoulder 36 equivalent to the shoulder 32 of the healing cap 30 for engaging the annular recessed groove 23 of the implant 12 as discussed in connection with FIG. 2. The post abutment 20 is preferably also formed with a collar 39 particularly when the post abutment 20 is to be preangulated. The collar 39 abuts the upright section 17 of the implant 12. The post abutment is preangulated at a fixed angle relative to the longitudinal axis of the implant to achieve parallelism with adjoining teeth in the mouth of the patient. A plurality of fixed pre-angulated post abutments 20 at different angles preferably between 0° to 30° to the central axis of the implant provides the dentist with an adequate selection of angles to achieve parallelism with adjoining teeth in the mouth of the patient. After selecting a desired pre-angulated post abutment 20 the post abutment 20 is then further adjusted into position for proper alignment with adjoining teeth by turning the distal end 38 around its central axis. Thereafter the post abutment 20 is cemented in place to the implant 10.

A variation of a post abutment design of FIG. 4 is shown in FIG. 17 in which the post abutment 80 has a proximal end 81 and a distal end 82. The distal end 82 is adapted to be fitted into the cavity 22 formed in the implant body 12. The abutment 80 may include an annular shoulder 36 equivalent to the annular shoulder 36 in FIG. 4. A shaft 84 is threadably connected into a threaded opening 85 in the abutment 80. The threaded opening 85 should be formed at any desired angle to the longitudinal axis of the abutment so that the shaft 84 will always extend ninety degrees from the face 86 of the abutment 80. The dotted lines about the shaft 84 in FIG. 17 show different position of the shaft 84 forming different angles between the threaded opening 85 and the longitudinal axis of the abutment. In this way a porcelain superstructure such as 18 in FIG. 4 may be formed over the shaft 84 with the shaft 84 aligned to achieve parallelism with adjoining teeth in the mouth of the patient. Before forming the porcelain superstructure over the shaft 84 a fused aluminum oxide sleeve 87 may be placed thereon to circumvent metal shadows particularly for anterior teeth.

Another embodiment of the two component implant of the present invention, preferably for use in cases where minimum vertical height of bone is available, is illustrated in FIGS. 5 through 7. In the embodiment of FIG. 5 an implant 40 is shown comprising a shaft 41 with a vertical height no greater than about 6 mm so that it will not involve contact with the maxillary sinus or the mandibular nerve. This implant embodiment is designed for use in the posterior portion of the mandible and maxilla, where their is minimum vertical height of bone. The shaft 41 of the implant 40 has a beveled collar 43 extending superiorly from the shaft 41 with a smooth polished outer surface. The exterior surface of the implant 41 may have a plurality of serrations 42 which are spaced longitudinally apart along the height of the implant body 41 to facilitate the seating of a plasma sprayed coating of hydroxyl apatite "HA" before the implant 40 is press fitted into a receptor site 44 formed in the jawbone 14 to receive the implant 40.

The implant 40 may be cylindrical or tapered in a shape similar to the geometry of the implant 10 and may be of a similar composition preferably of titanium metal. A plurality of projections 46 extend laterally from a position adjacent the upper end of the body 41 in a spider like arrangement and may terminate to form a plurality of bent outer tips 47 directed downwardly to engage openings 48 formed in the jawbone 14 surrounding the receptor site 44. Alternatively, the outer projections 46 may be straight and not form bended tips 47. In FIG. 7 a pair of implants 40 are shown inserted in the jawbone 14 in tandem to one another so that the projections 46 from each implant 40 mesh in a gear-like arrangement. The projections 46 should lie on the subperiosteal surface of the jawbone 14 at the interface between the jawbone 14 and mucosal tissue 45 as shown in FIG. 6. During the healing period ossiointegration will occur to cover the projections 46. The plurality of bent outer tips 47 which extend into the jawbone 14 become integrated with the bone to form a unitary endosseous implant. A receptor site is formed in the jawbone 14 to receive each implant 40 using a drill in the same fashion as the receptor site formed in the jawbone 14 of FIG. 2. A single tool may be used to form the receptor hole and multiple surrounding openings 48 into which the tips 47 are placed. The projections 46 and depending tips 47 give the implant 40 lateral stability to anchor the short body 41 of the. implant 40 in the jawbone 14 throughout the healing period and afterwards.

During the healing period a healing cap 30 as shown in FIG. 2 is inserted into the cavity 22. The cavity 22 formed in the implant body 41 has a recessed annular groove 23 which interlocks with the complementary annular shoulder 32 of the healing cap 30 shown in FIG. 2. After the healing cap is removed from the cavity 22 a post abutment 52 as shown in FIG. 6 is seated in the cavity 22 and cemented in place. The post abutment 52 is constructed similarly to the post abutment 20 of FIG. 4 and may include the collar 39 of FIG. 4 to facilitate formation of a plurality of fixed preangulated post abutments 54 at different typical angles preferably between 0° to 30° to the central axis of the implant similar to preangulated post abutments 20. A porcelain superstructure is formed over the preangulated proximal end 54 of the post abutment 52 before the post abutment 52 is cemented in place following conventional practice.

The projections 46 extending from the implant 40 distribute the load from biting forces over a relatively broad subperisteal jawbone surface. The bent ends 47 of the implant 40 provide stability to lateral forces, since the perimeter is supported against and/or within the cortical bone. The implant 40 requires only one surgical procedure without the necessity for an impression.

The body 12 of each of the implant embodiments of the present invention may include a modified distal end constuction as shown in FIGS. 8–11 inclusive. In this embodiment the distal end 60 of the implant 12 contains a hollow area 61. A plurality of slitted sections 63 having a shape 62 corresponding to an inverted "V" are formed in the distal end 60 of the implant 12. The slitted sections 63 surround the hollow area 61 and extend lengthwise substantially parallel to the longitudinal axis of the implant. Each section 63 has an open ended tip 64 which is slightly bent in the lateral direction to facilitate crimping the sections 63 of FIG. 9 toward one another into the configuration shown in FIG. 11. With the tips 64 crimped as shown in FIG. 11 the hollow area 61 is substantially closed at the bottom end 66 of the implant 12. A bone morphogenic protein 67 which is known to facilitate bone osseointegration is inseted into the area 61 of the implant 12. Any known bone morphogenic protein 67 may be used and may be combined with collagen in a micro or macro encapsulated form to be absorbed by receptor cells once introduced into the surrounding bone. The distal end 60 of the implant should also have a plurality of openings 65, preferably four or more, laterally extending through the sections 63 into the area 61. Use of the hollow area 61 at the distal end of the implant as a reservoir reservoir for a gel or for micro or macro encapsulation of a bone morphogenic protein 67 is a unique feature of this invention.

In addition a grooved pathway 69 may be formed as shown in FIG. 8 in the implant 12 extending preferably from the openings 65 upwardly to the upright section 17 of the implant 12. The combination of openings 65 and the grooved pathways 69 provide a path for movement of the bone morphogenic protein 67 from the area 61 over the surface of the implant 12 allowing the bone morphogenic protein 67 to surround the implant 12 after it is implanted. The bone morphogenic protein 67 may be injected into the area 61 or may be placed in a porous vessel or bag 68 which is inserted into the area 61 before crimping the ends 64. The grooved pathway 69 functions as a feeder groove to a groove 79 surrounding the collar 17 of the implant 12 as shown in FIG. 8 to control die back at the occlusal or incisal aspect of the bone where the implant enters the bone.

Another implant design in accordance with the present invention which is designed primarily for use in the posterior portion of the mandible and/or maxilla where the jawbone is narrow but sufficiently deep to accommodate a long shaft is shown in FIG. 16 in which the implant 55 is a solid structure combining an elongated narrow gauge shaft 56 of at least between 18–22 mm adapted for insertion into an elongated cavity (not shown) formed in the jawbone and a post abutment structure 57 extending from the shaft 56 as an integral unit. The post abutment structure 57 may be preangulate to define a fixed pre-angulated post abutment at any desired angle of preferably between 0° to 30° to the central axis of the implant. This narrow gauge implant 55 may be used as a provisional implant or an a permanent implant.

A further embodiment of the present invention is shown in FIGS. 12–15 respectively. in this embodiment the implant system of the present invention comprises an implant 71 which is implanted in the upper or lower jawbone of a patient and a male plug 78 representing an abutment which is permanently affixed to a denture 72 to permit the denture 72 to be removably attached to the upper or lower jawbone containing the implant 71. In FIG. 12 the denture 72 is shown adapted for removable attachment to the lower jawbone 14 containing an implant 71 and in FIG. 14 the denture 72 is shown affixed to the lower jawbone 14 by the interlocking of the implant 71 and the male plug 78. Although one implant 71 will satisfy the requirements of this embodiment of the present invention two or more implants 71 are preferred. Each implant 71 as more fully shown in FIGS. 13 and 15 has a shaft portion 12 directly corresponding to the body 12 of the implant 10 of FIG. 1. The length of the shaft 12 can also be reduced to conform to the length of the shaft 41 of the implant 40 of FIG. 5. The shaft 12 of the implant 71 includes a beveled collar 73 extending superiorly from the shaft and a substantially upright section 74 of substantially cylindrical geometry at its proximal end. A threadless cavity 76 is formed extending from its proximal surface partly into the implant shaft 12 to a desired depth beneath the occlusal surface of the jawbone 14. The cavity 76 has a substantially spherical shape forming a spherically shaped socket into which the male plug 78 extending from the denture 72 is mounted. The male plug 78 may be permanently affixed to the denture 72 in any conventional fashion such as by insertion into an opening formed in the denture which is then closed using an adhesive cement or by molding the denture 72 with the male plug affixed thereto. Alignment between the male plug 78 and implant 71 is preestablished before the implant 71 is implanted in the jawbone 14 so that insertion of the male plug 78 into the implant 71 automatically maintains the denture 71 in a desired position on the jawbone 14. The male plug 78 has a substantially spherical shape which is complementary to the spherical geometry of the cavity 76 to cause interlocking engagement of the male plug 78 and the cavity 76. The male plug 78 can be manually disengaged from the cavity 76 by lifting the denture off the jawbone 14.

What I claim is:

1. A press fit dental implant system comprising an implant having an apical portion with a straight section and a tapered section for insertion into a alveolar receptor site formed in the jawbone to receive the implant with the implant having an occlusal end and a proximal end, a collar having a beveled section extending superiorly from the apical portion, a threadless cavity extending interiorly from the occlusal end of the implant partially into its apical portion with the threadless cavity having a conical area within the beveled section of the collar and a recessed annular groove formed in said conical area below the occlusal end of the implant, a removable healing cap adapted to be placed into the threadless cavity of said implant with said healing cap having a beveled section contoured to match the beveled section in said collar, an annular resilient shoulder projecting from its beveled area to engage said recessed annular groove in said threadless cavity for forming a sealed interlock during an extended healing period, a domed top having at least one depressed area adapted to enable the top of the healing cap to be gripped mechanically or with the use of fingers for removal of the healing cap and a post abutment member for insertion into the threadless cavity of the implant after removal of the healing cap.

2. A dental implant system as defined in claim 1 wherein said post abutment member has a distal end portion adapted to be inserted into said threadless cavity after removal of said healing cap and a proximal end portion for connection to a dental prosthesis.

3. A dental implant system as defined in claim 2 wherein said proximal end portion of said abutment member is pre-angulated to form an angle of between 0° to 30° relative to the longitudinal axis of the implant to achieve parallelism with adjoining teeth in the mouth of the patient.

4. A dental implant system as defined in claim 3 further comprising a plurality of serrations formed around the circumference of the incisal portion of the implant in a spaced apart relationship which extend over a section of the vertical height of the implant.

5. A dental implant system as defined in claim 4 further comprising a plasma sprayed coating of hydroxyl apatite seated within said serrations to protect against delamination.

6. A dental implant system as defined in claim 2 wherein said proximal end portion of said abutment member has an opening at a predetermined angle to the longitudinal axis of the implant for receiving a removable elongated shaft to achieve parallism with adjoining teeth.

7. A dental implant system as defined in claim 6 wherein said shaft threadably engages said proximal end portion of said post abutment.

8. A dental implant system as defined in claim 2 wherein said healing cap has a top end with at least two depressed openings to receive a tool for removing said cap from said cavity.

9. A dental implant system as defined in claim 2 wherein the distal end of said incisal portion has a plurality of projections surrounding an open area with the projections adapted to form an enclosure surrounding said open area adapted to receive bone morphogenic protein material.

10. A dental implant system as defined in claim 9 further comprising laterally spaced openings in the projections to permit the bone morphogenic protein to escape the enclosed area.

11. A dental implant system comprising an implant having an apical portion with a vertical height of less than about 6 mm for insertion into a very shallow bone receptor site formed in the jawbone of the patient, a coronal end section extending superiorly from the proximal end of the apical portion and a plurality of projections laterally extending from the apical portion in a spider like arrangement which initially cover a broad subperiosteal surface at the interface between the jawbone and mucosal tissue to give the implant lateral stability against lateral forces, wherein each of said plurality of projections have an outer tip at the terminal end of the projection extending downwardly at substantially ninety degrees from each of said projections and being adapted to engage openings formed in the jawbone surrounding said bone receptor site for providing lateral resistance to movement of the implant.

12. A dental implant system adapted to interlock a denture to a jawbone with the dental implant system comprising an implant having an incisal portion for insertion into an alveolar receptor site formed in the jawbone to receive the implant, a collar having a beveled section extending superiorly from the incisal portion, a threadless cavity extending from the occlusal end of the implant partially into said embedded incisal portion having a spherically shaped area adjacent the proximal end of the incisal portion and a male plug having a section adapted to be affixed to the denture with the male plug extending from the denture in alignment with the implant and a section for insertion into the cavity of the a vertical height of less than about 6 mm for insertion into a very shallow bone receptor site formed in the jawbone of the patient, a plurality of projections laterally extending from a position near the apical end of the implant in a spider like arrangement which initially cover a broad subperiosteal surface at the interface between the jawbone and mucosal tissue to give the implant lateral stability against lateral forces.

13. A dental implant system as defined in claim 12 wherein said plurality of projections terminate to form a plurality of outer tips bent downwardly to engage openings formed in the jawbone surrounding said bone receptor site. A dental implant system as defined in claim 12 wherein said incisal section X includes a threadless cavity into which a healing cap is removably inserted, A dental implant system as defined in claim 4 wherein said threadless cavity has an annular recessed groove and said healing cap has a complimentary annular shoulder for forming an interlocking seal within said cavity to prevent microbial leakage.

14. A dental implant system comprising an implant having an apical portion for insertion into a alveolar receptor site formed in the jawbone to receive the implant, a collar having a beveled section extending superiorly from the apical portion, a cavity extending from the occlusal end of the implant partially into said embedded apical portion for receiving a post abutment member and a distal section having a hollow area opening distally into the jawbone for forming an enclosure adapted for insertion of a bone morphogenic protein material wherein said distal section of the implant has a plurality of slitted projections surrounding said hollow area and extending lengthwise to permit the distal end to be crimped about the inserted bone morphogenic protein.

15. A dental implant system as defined in claim 14 further comprising a plurality of grooved pathways extending from said distal section to said collar and a plurality of openings through said distal section into said hollow area to permit the bone morphogenic protein material to pass upwardly over the exterior surface of the implant after insertion of the implant.

\* \* \* \* \*